United States Patent [19]

Lagana et al.

[11] 4,235,816
[45] Nov. 25, 1980

[54] INTEGRATED AMMONIA-UREA PROCESS

[75] Inventors: Vincenzo Lagana, Milan; Francesco Saviano, Segrate, both of Italy

[73] Assignee: Snamprogetti S.p.A., Milan, Italy

[21] Appl. No.: 18,729

[22] Filed: Mar. 8, 1979

[51] Int. Cl.$^3$ .......................................... C07C 126/00
[52] U.S. Cl. .................................................... 564/72
[58] Field of Search .................. 562/555; 260/555 A; 423/359

[56] References Cited

U.S. PATENT DOCUMENTS

| | | | |
|---|---|---|---|
| 3,120,563 | 2/1964 | Bongard | 260/555 A |
| 3,310,376 | 3/1967 | Cook | 260/555 A |
| 3,674,847 | 7/1972 | Kassenbrood | 562/555 |
| 3,684,442 | 8/1972 | Konoki | 260/555 A |
| 4,012,443 | 3/1977 | Bonetti | 260/555 A |
| 4,013,718 | 3/1977 | Guadalupi | 260/555 A |
| 4,138,434 | 2/1979 | Lagana | 260/555 A |

Primary Examiner—Brian E. Hearn
Attorney, Agent, or Firm—Morgan, Finnegan, Pine, Foley & Lee

[57] ABSTRACT

An integrated ammonia-urea process is disclosed which uses as the starting gas mixture a stream coming, for example, from steam reforming of hydrocarbons, carbon dioxide being stripped from the stream by the action of a very concentrated ammonia solution (above 70% by wt) first and the the action of an ammoniated solution of ammonium carbonate secondly, a solution of ammonium carbamate being obtained together with a gas stream composed of nitrogen and hydrogen; sending the carbamate solution to the urea reactor, discharging from the urea reactor the urea solution containing unconverted carbamate and excess ammonia, decomposing said carbamate and sending evolved ammonia to the urea reactor again along with carbon dioxide, discharging the urea solution having now 50% of the original carbamate to an adiabatic stripper in which the stripping gas is essentially composed of hydrogen and nitrogen, removing ammonia and carbon dioxide with water from the adiabatic stripper and condensing ammonia and carbon dioxide by heat exchange, sending the stream of hydrogen and nitrogen to methanization and ammonia synthesis and concentrating the urea solution directly until obtaining a urea melt.

3 Claims, 1 Drawing Figure

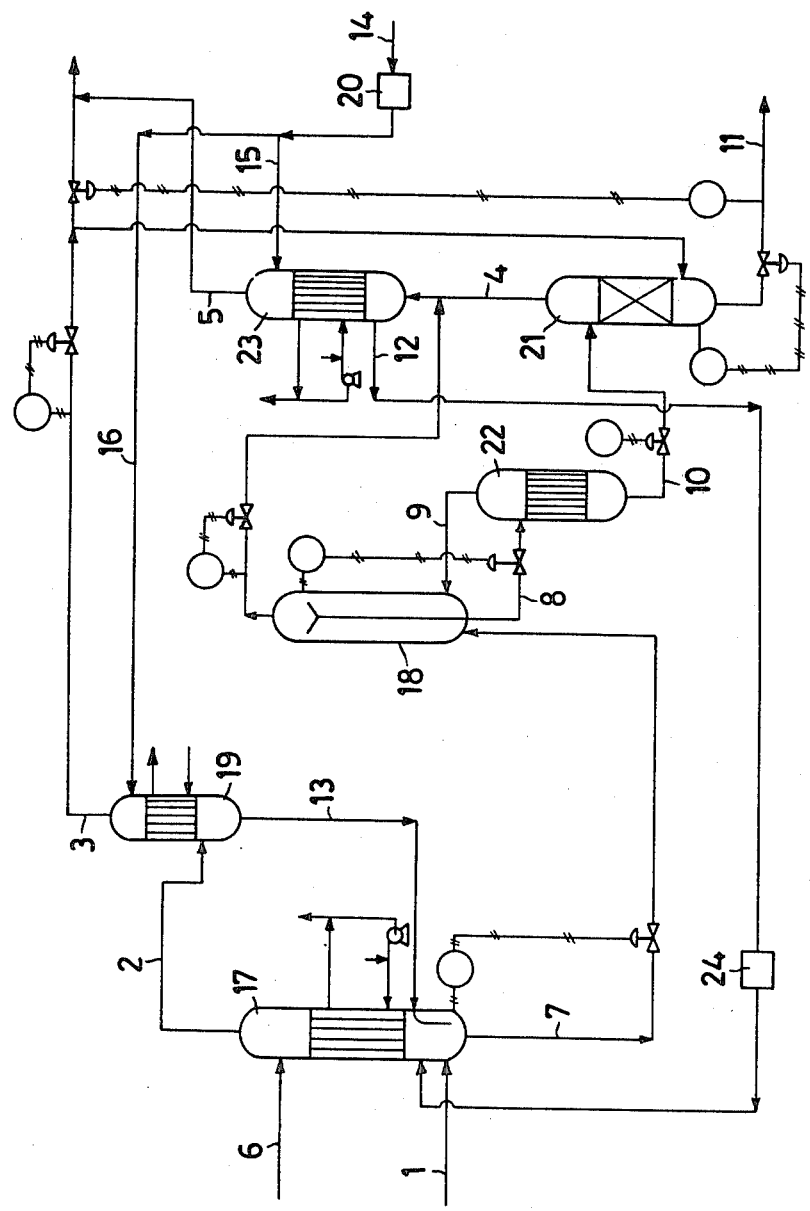

INTEGRATED AMMONIA-UREA PROCESS

This invention relates to an integrated ammonia-urea process.

A number of integrated processes are known for the synthesis of urea in combination with the synthesis of ammonia.

One of these is, more particularly, the one disclosed in the U.S. Patent application Ser. No. 857,185 filed on Dec. 2, 1977, now U.S. Pat. No. 4,138,434.

The method described in the patent application aforementioned comprises the steps of feeding to a urea-synthesis reactor a stream of anhydrous ammonia and/or an aqueous solution of ammonia and a stream containing ammonium carbamate, reacting carbon dioxide with the ammonia in the urea-synthesis reactor, discharging from the urea-synthesis reactor a solution of urea which contains unconverted ammonium carbamate, thermally decomposing about the 50% of the carbamate contained in the urea solution and separating the decomposition products, recycling the decomposition products to the urea-synthesis reactor, adiabatically decomposing, i.e. without administering heat from an external source, the ammonium carbamate still contained in the urea solution in an adiabatic stripper in which there is introduced, as the stripping agent, the gas stream obtained by steam-reforming or partial oxidation of liquid or gaseous hydrocarbons, essentially composed of $CO_2$, $N_2$ and $H_2$ to be used generally for the synthesis of ammonia, removing from the adiabatic stripper both $CO_2$ and the $NH_3$ derived from the decomposition of the residual ammonium carbamate and the stripping agent, feeding the gas mixture aforesaid to a $CO_2$-absorber in which the $CO_2$ is absorbed by an ammoniacal solution thus obtaining a stream containing ammonium carbamate to be fed to the urea-synthesis reactor, discharging from the adiabatic stripper the solution of urea substantially devoid of carbamate, and sending the solution of urea through subsequent treatments of low-pressure decomposition and concentration under vacuum.

A shortcoming of the method outlined above is that the content of $CO_2$ in the solution going from the bottom of the adiabatic stripper to the low-pressure decomposition stage, is rather high (10% to 15% by wt.) the result being the necessity of employing an oversized decomposition stage and an increase in the consumption in the same apparatus.

On the other hand, the run of the adiabatic stripper according to the patent application aforementioned was bound to the use of $CO_2$ among other stripping agents, inasmuch as the $CO_2$ permitted, by its partial reaction with the ammonia contained in the urea solution, the supply of at least partially, the heat which is required for the decomposition of the ammonium carbamate contained in the urea solution. Regrettably, as outlined above, the $CO_2$ content remains high so that the low-pressure decomposition stage must be significantly oversized.

It has been surprisingly found that it is possible to dispense with $CO_2$ as the stripping agent, and consequently to have an end product substantially free of $CO_2$ without giving up the adiabatic stripping.

This achievement is made possible by selecting appropriate ratios between $H_2O$ and $CO_2$ and between $NH_3$ and $CO_2$ in the urea synthesis reactor.

An object of the present invention is to provide an integrated ammonia-urea process comprising the following stages:

(a) to send the gaseous stream as obtained from steam-reforming or partial oxidation of liquid or gaseous hydrocarbons which make up the raw gas stream for the synthesis of ammonia, and which essentially comprise $H_2$, $N_2$ and $CO_2$, to a $CO_2$-absorption system using a concentrated aqueous solution of ammonia and which is more particularly composed of two serially arranged discrete absorption stages, in the first of which the absorbing liquor is a concentrated aqueous solution of ammonia (concentration above 70% by wt of ammonia, 80% being preferred), whereas in the second stage the absorption liquor is an aqueous ammoniated solution of ammonium carbonate as obtained from the low-pressure decomposition stage, or, in the case in which the latter is not provided, from the stage of decomposition under vacuum of the urea solution;

(b) to discharge from the $CO_2$-absorption section a gas stream which is essentially composed of $N_2$ and $H_2$ (with possible traces of $NH_3$ and $CO_2$) together with a liquid stream which essentially comprises an aqueous solution of ammonium carbamate;

(c) to feed the aqueous solution of ammonium carbamate to a urea-synthesis reactor wherein the ammonium carbamate is partially converted into urea;

(d) to discharge from the urea-synthesis reactor an aqueous solution of urea which contains the unconverted ammonium carbamate and the excess of ammonia over the stoichiometric amount and possibly a gaseous stream from the reactor top, the stream essentially comprising inerts and a certain amount of $NH_3$ and $CO_2$;

(e) to feed the aqueous solution of urea from stage (d) to a decomposer in which the ammonium carbamate is decomposed into ammonia and carbon dioxide, the latter being both withdrawn from said decomposer together with the water which evaporats off, to be recycled in the vapor phase to the ureasynthesis reactor;

(f) to discharge from the decomposer an aqueous solution of urea which contains about the 50% of the carbamate originally contained in the urea solution exiting the synthesis reactor and to feed said aqueous solution to an adiabatic stripper wherein it is employed as a stripping agent of the gaseous stream of (b) above;

(g) to discharge through the bottom of the adiabatic stripper the solution of urea substantially devoid of ammonium carbamate, and to discharge from the top of the stripper the stripping agent ($N_2 + H_2$) with the products of decomposition of the carbamate ($NH_3 + CO_2$) and the evaporated water;

(h) to introduce the gaseous mixture withdrawn from the top of the adiabatic stripper to a condenser wherein the ammonia and the carbon dioxide are condensed by cooling as a result of an indirect heat exchange with a cold fluid in the presence of an ammoniated solution of ammonium carbonate coming from the low-pressure decomposition stage whereas the stream with $H_2$ and $N_2$ is discharged at the top and fed, upon methanization, to the ammonia synthesis together with the inert gases $N_2$ and $H_2$ exiting the $CO_2$-absorption system;

(i) to send the condensate from (h) to the $CO_2$-absorber;

(l) to send the urea solution of stage (g) to the vacuum concentration stage either directly or through a previous low-pressure decomposition stage (4 to 5 atmospheres), there being obtained both from the head of the low-pressure decomposition stage and from the vacuum concentration stage a gas mixture composed of ammonia, CO₂ and water, which, when condensed, is the ammoniated solution of ammonium carbonate to be used for the steps (a) and (h), melted urea being obtained through the bottom of the concentration stage under vacuum.

BRIEF DESCRIPTION OF THE DRAWING

The method according to the present invention will now be illustrated in a preferred embodiment with the aid of the accompanying drawing.

The raw gas which essentially comprises $CO_2$, $N_2$ and $H_2$, is sent, after having been compressed, via the piping 1, to the $CO_2$-absorber 17, wherein the absorbing liquid is mainly composed of an aqueous solution of ammonia which comes via the piping 6 from an ammonia synthesis reactor, the ammonium carbamate coming from the absorber 17 is sent via the piping 7 to the ureasynthesis reactor 18.

The decarbonated gas exits the absorber 17 and, via the piping 2, goes to the $NH_3$-stripping condenser 19, in which $NH_3$ is absorbed by an aqueous solution of ammonium carbonate 14 coming, through the pipe 16, from a low-pressure liquor-recovering section by means of the pump 20.

The ammoniated solution formed at 19 is sent via the piping 13 to the absorber 17.

The purified gas is sent via the piping 3 to the adiabatic stripping column 21 which is fed via the piping 10, with the urea solution coming from the carbamate decomposer 22. The gas stream exits the column 21 and, via the piping 4, is fed to the carbamate condenser 23 where it is combined with an aqueous solution of ammonium carbonate 14, as fed via the pump 20 and the piping 15 from the low-pressure liquor-recovery section. The carbamate produced at 23 is sent via the piping 12 and the pump 24 to the $CO_2$-absorber 17.

The purified gases exiting the condenser 23 are sent via the piping 5 to methanization and, therefrom, to the ammonia synthesis in which an ammoniated solution is produced to be sent to the absorber 17 via the piping 6 as outlined above.

The carbamate solution, via the piping 7, is sent to the urea reactor 18 in which dehydration of the carbamate into urea takes place. The thusly obtained solution of urea reaches, via the pipe 8, the carbamate decomposer 22 wherein the carbamate is decomposed into $CO_2$ and $NH_3$ and these latter are recycled via the piping 9 to the reactor 18.

The urea solution, along with the carbamate which has not been decomposed, is sent via the piping 10 to the adiabatic stripping column 21 which has been described above.

The solution of urea exiting the bottom of the column 21 is sent via piping 11 to the vacuum evaporation section under vacuum (not shown), wherein it is treated in the conventional manner.

It is quite surprising that, when operating with the process according to the present invention, it becomes possible to obtain at the exit of the adiabatic stripper a solution of urea which is so highly concentrated that it may be sent directly to the final treatment under vacuum. By so doing, considerable advantage is achieved in that the expensive operations of decomposition of the undecomposed carbamate under medium (18 atm) and low (4.5 atm) pressures are dispensed with and so is the recondensation of the produced vapors.

This is contrary to the teachings of the prior art, according to which the solution to be sent to evaporation under vacuum is obtained at the expense of a considerable power usage.

All that which has been described above requires in the urea reactor a selection of the ratio of $H_2O$ to $CO_2$ within the range of from 0.9 and 1.3, to 1.0 the preferred value being 1.1 to 1.0, and of the ratios of $NH_3$ to $CO_2$ comprised between 4.5 and 6.5 to 1.0, the preferred value being 5.5 to 1.0.

A modification which has not been shown in the drawings consists in using, instead of the pump 24 for recycling the carbamate towards the absorber 17, an ejector, the working fluid for which is the 80% ammoniated solution coming from the ammonia synthesis reactor via the piping 6.

As regards the pressures, the method according to the present invention works under a pressure comprised between 100 kg/cm² and 300 kg/cm², a pressure which is virtually equal to that at which the ammonia synthesis reactor operates, and in such a case a pump may be required for sending the ammoniated solution from the ammonia synthesis reactor to the cycle described above, or under a pressure which is from 10 kg/cm² to 100 kg/cm² below the pressure at which the ammonia synthesis reactor works, and in this case the pump can be dispensed with.

A practical example will now be given in order that the invention may be better illustrated but without limiting it in any way.

EXAMPLE

Reference will be had to the single FIGURE of the drawing.

TABLES 1 and 2 report the working conditions, the concentrations and the rates of flow.

TABLE 1

| Drawing item | 1 | | 3 | | 4 | | 5 | | 6 | | 7 | | 8 | |
|---|---|---|---|---|---|---|---|---|---|---|---|---|---|---|
| FLUID TYPE | SYNGAS + $CO_2$ | | SYNGAS + $NH_3$ | | HEAD (21). | | SYNGAS + $NH_3$ | | AMMONIATED SOLN. | | CARBAMATE SOLN. | | UREA SOLN. | |
| Temp. °C. | 135 | | 35 | | | | | | | | 140 | | 185 | |
| Press.atm | 200 | | 198.5 | | ~194.7 | | ~194.2 | | | | 200 | | | |
| | FLOW VOL. | | FLOW VOL. | | FLOW VOL. | | FLOW VOL. | | FLOW,WT | | FLOW WT | | FLOW WT | |
| | norm. m³/h | % vol. | norm. m³/h | % vol. | Norm m³/h | % vol. | norm. m³/h | % vol. | kg/h | % wt. | kg/h | % wt. | kg/h | % wt. |
| $N_2$ | 17173 | 20 | 17173 | 22 | 17173 | 12.5 | 17173 | 23 | | | | | | |
| $H_2$ | 53237 | 62 | 53237 | 68 | 53237 | 38.7 | 53237 | 73 | | | | | | |
| $CO_2$ | 15458 | 18 | | | 3247 | 2.4 | | | | | 37909 | 30.9 | 14051 | 8.81 |
| $NH_3$ | | | 7823 | 10 | 63882 | 46.4 | 2998 | 4 | 25926 | 80 | 68954 | 56.3 | 71178 | 44.63 |
| $H_2O$ | | | | | | | | | 6483 | 20 | 15687 | 12.8 | 32573 | 20.43 |
| UREA | | | | | | | | | | | | | 41667 | 26.13 |

TABLE 1-continued

| TOTAL | 85868 | 100 | 78233 | 100 | 137539 | 100 | 73408 | 100 | 32409 | 100 | 122550 | 100 | 159469 | 100 |

SYNGAS = synthesis gas.

TABLE 2

| Drawing item | 9 | | 10 | | 11 | | 12 | | 15 | |
|---|---|---|---|---|---|---|---|---|---|---|
| FLUID TYPE | HEAD (22) | | UREA SOLN. | | UREA SOLN. | | CARBONATE SOLN. | | CARBONATE SOLN. | |
| Temp. °C. | 195 | | 210 | | 110 | | 60 | | | |
| Press.atm | | | 196.5 | | | | 195 | | | |
| | FLOW | WT. | FLOW | WT. | FLOW | WT. | FLOW | WT. | FLOW | WT. |
| | kg/h | % wt | kg/h | % wt | kg/h | % wt | kg/h | % wt | kg/h | % wt |
| $N_2$ | | | | | | | | | | |
| $H_2$ | | | | | | | | | | |
| $CO_2$ | 6698 | 18.1 | 7353 | 6 | 933 | 1.4 | 7080 | 11.1 | 660 | 18 |
| $NH_3$ | 25835 | 70 | 45343 | 37 | 2177 | 3.3 | 48422 | 75.6 | 1540 | 42 |
| $H_2O$ | 4386 | 11.9 | 28187 | 23 | 21119 | 32.1 | 8535 | 13.3 | 1467 | 40 |
| UREA | | | 41667 | 63.2 | 41667 | 63.2 | | | | |
| TOTAL | 36919 | 100 | 122550 | 100 | 65896 | 100 | 64037 | 100 | 3667 | 100 |

We claim:

1. An integrated ammonia-urea process comprising the steps of:
   (a) Sending the gaseous stream obtained from steam reforming or partial oxidation of liquid or gaseous hydrocarbons, containing $H_2$, $N_2$ and $CO_2$, to a $CO_2$-absorption system in which $CO_2$ is absorbed by a concentrated aqueous solution of ammonia,
   (b) discharging from the $CO_2$-absorption system a gaseous stream composed essentially by $H_2$ and $N_2$ and a liquid stream essentially composed by an aqueous solution of ammonium carbamate,
   (c) feeding with the aqueous solution of ammonium carbamate a urea synthesis reactor wherein the carbamate is partially converted into urea,
   (d) discharging from the urea synthesis reactor an aqueous solution of urea containing the unconverted ammonium carbamate and the excess of ammonia relative to the stoichiometric amount,
   (e) feeding the aqueous solution of urea which contains the uncoverted carbamate to a decomposer and thermally decomposing therein about the 50% of said carbamate, discharging a solution of urea containing carbamate and the decomposition products, the latter being recycled in the vapor phase to the urea synthesis reactor,
   (f) decomposing the carbamate contained in the solution of urea exiting the decomposer of the carbamate of stage (e) in an adiabatic stripper in which the gaseous stream of stage (b) is used as the stripping agent, a urea solution substantially devoid of carbamate being obtained at the bottom, whereas the decomposition products, the stripping agent and the evaporated water are obtained at the stripper head,
   (g) condensing the decomposition products and the evaporated water in the presence of an ammoniated solution of ammonium carbonate by indirect heat exchange with a cold fluid, the inert gases ($H_2+N_2$) to be used for the ammonia synthesis upon methanization being discharged through the condenser head,
   (h) sending the condensate as produced in stage (g) to the $CO_2$-absorption stage,
   (i) sending the solution of urea exiting the bottom of the adiabatic stripper to a concentration stage and discharging melted urea from the latter, wherein, in the urea reactor the ratio of $H_2O$ to $CO_2$ being in the range of from 0.9 and 1.3 to 1 and the ratio of $NH_3$ to $CO_2$ being in the range of from 4.5 and 6.5 to 1.

2. A process according to claim 1 wherein the $CO_2$-absorption system is composed of two serially arranged absorption stages, in the first of which the absorption liquor is a concentrated aqueous solution of ammonia containing more than 70% by weight of ammonia, and in the second of which the absorption liquor is an ammoniated aqueous solution of ammonium carbonate.

3. A process according to claim 1 wherein the ratio of $H_2O$ to $CO_2$ is 1.1 to 1.0, and the ratio of $NH_3$ to $CO_2$ is 5.5 to 1.0.

* * * * *